United States Patent [19]

Noda et al.

[11] 4,393,076

[45] Jul. 12, 1983

[54] ANTI-INFLAMMATORY AND ANALGESIC GEL COMPOSITION

[75] Inventors: Kanji Noda, Chikushino; Akira Nakagawa; Tetsuya Yamagata, both of Tosu; Hiroyuki Ide, Fukuoka, all of Japan

[73] Assignee: Hisamitsu Pharmaceutical Co., Inc., Tosu, Japan

[21] Appl. No.: 348,887

[22] Filed: Feb. 16, 1982

Related U.S. Application Data

[63] Continuation-in-part of Ser. No. 260,633, May 5, 1981, abandoned.

[30] Foreign Application Priority Data

May 14, 1980 [JP]  Japan .................................. 55/65066
May 14, 1980 [JP]  Japan .................................. 55/65067

[51] Int. Cl.$^3$ .............................................. A61K 31/19
[52] U.S. Cl. ..................................................... 424/317
[58] Field of Search ......................................... 424/317

[56]  References Cited

U.S. PATENT DOCUMENTS 4,230,724 10/1980 Cooper et al. ...................... 424/317

Primary Examiner—Stanley J. Friedman
Attorney, Agent, or Firm—Jordan and Hamburg

[57]  ABSTRACT

An anti-inflammatory analgesic gel composition comprising (1) ketoprofen and/or flurbiprofen as the effective ingredient, as well as (2) a glycol, lower alcohol, water and/or a mixture of a lower alcohol with water, (3) a gel-forming agent and, if desired, (4) a solubilizing agent and/or non-ionic surface-active agent as the ingredients of a gel base for the gel composition.

15 Claims, No Drawings

ANTI-INFLAMMATORY AND ANALGESIC GEL COMPOSITION

This is a Continuation-in-Part application of Ser. No. 260,633, filed May 5, 1981, now abandoned.

This invention relates to an anti-inflammatory and analgesic gel composition comprising ketoprofen and/or flurbiprofen as the effective ingredient.

Ketoprofen and flurbiprofen are phenylpropionic acid derivatives represented respectively by the formulae (I) and (II)

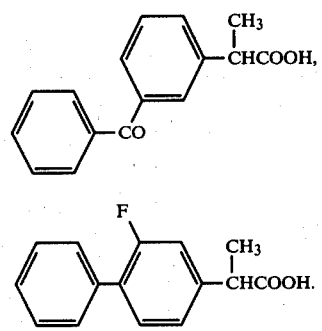

These compounds of the formulae (I) and (II) are a non-steroid type medicine having anti-inflammatory and analgesic activities and are generally used particularly for the remedy of chronic rheumatoid arthritis deformable arthritis and trauma, for relieving the pain and inflammation caused after having undergone an operation and for the cure of inflammatory diseases in various departments.

Conventional non-steroid type anti-inflammatory, analgesic medicines have been usually used in the form of capsules and tablets by oral administration and have clinically exhibited excellent results, while repeated oral administration of said medicines has raised problems as to the side reactions, such as gastrointestinal, hepatic and nephric troubles. Thus, in attempts to reduce such side reactions, suppositories and other preparations were tried to be produced with the result that satisfactory ones are not obtained yet.

Particularly the conventional non-steroid type, anti-inflammatory and analgesic medicines have generally been known to be extremely inferior in percutaneous absorption. So, most of these medicines were externally used in some cases but they did not exhibit satisfactory percutaneous absorption in these cases. In addition, there are very few medicines for external application which are useful enough from the view-point of topical effectiveness and safety.

In Japanese Laid-Open Patent application No. 53-81616 for example, there is disclosed an anti-inflammatory and analgesic ointment containing indomethacin, which ointment is the one developed as a medicine for the cure of inflammatory diseases in order to reduce the side reactions such as gastrointestinal troubles by the external and local use of the ointment. However, this ointment is also inferior in percutaneous absorption because of unsatisfactory discharge of the effective ingredient from the gel base of the ointment, has side effects such as cutaneous irritation, is not so developed as to cause no gastrointestinal troubles and, therefore, clinically raises many problems as to success of treatment; thus, the ointment is not such that has overcome the conventional drawbacks.

For the reasons mentioned above, there are now sought the development of anti-inflammatory, analgesic medicines for external use which have excellent percutaneous absorbability, medicinal efficacy and higher safety.

Indomethacin contained as the effective ingredient in the indomethacin-containing gel composition which has been compared with the gel composition of the present invention, and heretofore been widely used as an oral medicine and is equal or somewhat superior in anti-inflammatory analgesic action as an oral medicine to the effective ingredient of the composition of the present invention.

As indicated in, for example, "Japanese Journal of Pharmacology, 70(4) 543–569 (1974)", "Pharmacology and Remedy, 3(5) 828–835 (1975)", "Rheumatism 14(3) 279–286 (1974)" and "Diagnosis and New Medicines 17(3) 531–541 (1980)", indomethacin and ketoprofen (which is one of the effective ingredients of the gel composition of the present invention) were respectively orally administered to make a comparative test for anti-inflammatory action, analgesic and antipyretic action, central action, medicinal efficacy for chronic articular rheumatism, results of clinical study of chronic lumbaginous disease, and the like.

All these publications indicate that indomethacin is equal or slightly superior in medicinal efficacy to the effective ingredient of the composition of this invention when orally administered.

The present inventors, on the other hand, found that indomethacin which exhibits a satisfactory medicinal efficacy when orally administered as mentioned above will surprisingly not exhibit a satisfactory medicinal efficacy as compared with the effective ingredient according to this invention when used as an indomethacin-containing gel composition for external application to integument.

In contrast, the effective ingredient according to this invention which has been chosen by the present inventors after their intensive studies, will exhibit a marked medicinal efficacy and effect as compared with indomethacin when used as the effective ingredient-containing gel composition for external application to integument although said effective ingredient is equal or slightly inferior in efficacy to indomethacin when orally administered. It was found that particularly the effective ingredient according to this invention has excellent percutaneous absorbability, anti-inflammatory analgesic effect and higher safety.

It is seen from the foregoing that, in general, medicinal ingredients which are effective when orally administered are not necessarily effective when used as a gel composition for external application to integument and, therefore, they must be intensively studied to find their uses, especially their best uses, and solve pharmaceutical problems. Further, indomethacin is pharmaceutically disadvantageous in that it is unstable to alkalies, inferior in solubility in the gel base and apt to crystallize out, while the present inventors found that ketoprofen and flurbiprofen are each excellent in stability to and solubility in the gel base according to this invention and also found that the gel composition of this invention is excellent in feeling when in use. Thus, the present invention are based on these findings.

The gel compositions of this invention may be obtained by mixing together (1) ketoprofen and/or flurbiprofen, (2) a glycol, a lower alcohol, water or a lower alcohol-water mixture, (3) a gel-forming agent and, if desired, (4) a solubilizing agent and/or a non-ionic surface-active agent and then allowing the whole to gel. In addition, a neutralizing agent may be suitably incorporated depending on the kind of a gel-forming agent used.

More particularly, preferable glycols used in this invention include propylene glycol, butylene glycol, polyethylene glycol, polypropylene glycol, polyethylene glycol dodecyl ether and glycerine; and preferable lower alcohols used herein include ethanol, denatured ethanol, propanol and isopropanol. The lower alcohols are usually used with water in admixture or they are not used at all in some cases where other certain ingredients are used although water is used alone in these cases. In this invention, the glycol, the lower alcohol and water may be used in amounts by weight of 20-40%, preferably 5-35%, 0-60%, preferably 20-45%; and 20-55%, preferably 25-45%, respectively.

The gel-forming agents used herein include carboxyvinyl polymers, hydroxyethylcellulose, methylcellulose, carboxymethylcellulose, hydroxypropylcellulose and alginic acid-propylene glycol ester. They may preferably be used in such an amount that their final concentration is in the range of 0.5-5%, preferably 1-3%, by weight.

Further, organic amines usable for neutralizing the carboxyvinyl polymers preferably include triethanolamine, diethylamine, triethylamine, diisopropylamine and diisopropanolamine. These neutralizing agents may preferably be used in an amount by weight of 0.1-3%, preferably 0.4-2%. The amount thereof used may be controlled so that the gel composition of this invention is kept nearly neutral (preferably pH 4.5-7), more preferably at a pH of 5.0-6.5.

The solubilizing agents may preferably include propylene carbonate, diethyl sebacate, benzyl alcohol and diisopropyl adipate. They are preferably be used in amounts by weight of 0-20%, preferably 0-10% to solubilize ketoprofen and/or flurbiprofen.

The non-ionic surface-active agents used herein may preferably include sesquioleic acid sorbitan, trioleic acid sorbitan, monooleic acid sorbitan, monostearic acid sorbitan, monolauric acid sorbitan, monostearic acid polyethylene glycol, monooleic acid polyoxyethylenesorbitan, monolauric acid polyoxyethylenesorbitan, polyoxyethylenenonylphenyl ether, polyoxyethylenecetyl ether, polyoxyethylenelauryl ether and mixtures thereof. The surface-active agents may be used in amounts by weight of 0-15%.

Ketoprofen and flurbiprofen which is the effective ingredients of the gel composition of this invention may be used in an amount by weight of 0.5-10%, preferably 1-7%.

The ketoprofen- or flurbiprofen-containing gel compositions of this invention may be obtained, for example, by (A) swelling a gelling agent with water, (B) dissolving ketoprofen and/or flurbiprofen with a solubilizing agent, further dissolving the material (B) in a mixture of a glycol and a lower alcohol, adding the material (B) so further dissolved to the material (A) to form a mixture, incorporating the mixture with an amine and then allowing the whole to gel. In addition, the gel composition of this invention may also be obtained even in cases where the aforementioned procedure such as the order of incorporation of the ingredients, is somewhat changed.

The gel compositions of this invention so obtained will be stable when stored for a long time and will exhibit excellent anti-inflammatory and analgesic effects with high safety when applied to skins as evidenced by the following experiments.

This invention will be better understood by the non-limitative examples wherein all parts are by weight unless otherwise specified.

EXAMPLE 1

One and a half (1.5) parts of carboxyvinyl polymer (Carbopol 940 produced by Goodrich Chemical Co.) were swollen in 20 parts of water. Separately, 10 parts of propylene carbonate were mixed with 35 parts of propylene glycol to form a mixture in which 1 part of ketoprofen was dissolved. Then, 2 parts of hydroxypropylcellulose were dissolved in 20 parts of ethanol to form a solution which was added to the swollen carboxyvinyl polymer and agitated until the swollen polymer had been thoroughly hydrated. The polymer so hydrated was mixed with said solution of ketoprofen in the mixture of propylene carbonate and propylene glycol, incorporated with an aqueous solution of 0.2 parts of triethanolamine in 10.3 parts of water and then thoroughly agitated until the whole was made homogeneous, thereby to obtain an anti-inflammatory and analgesic gel composition.

EXAMPLE 2

Two parts of carboxyvinyl polymer (Hiviswako 104 produced by Wako Junyaku Kogyo Co., Ltd.) were swollen in 20 parts of water. Separately, 15 parts of propylene carbonate were mixed with 20 parts of propylene glycol to form a mixture in which 3 parts of ketoprofen were dissolved. Then, 2 parts of hydroxypropylcellulose were dissolved in 30 parts of ethanol and the resulting solution was added to said swollen carboxyvinyl polymer and agitated until the polymer had been entirely hydrated. The whole so agitated was incorporated with said solution of ketoprofen in the mixture of propylene carbonate and propylene glycol, further incorporated with a solution of 0.2 parts of triethanolamine in 7.8 parts of water and thoroughly agitated until the whole was made homogeneous thereby to obtain an anti-inflammatory and analgesic gel composition.

EXAMPLE 3

One and a half (1.5) parts of carboxyvinyl polymer (the same as that used in Example 1) were swollen in 20 parts of water. Separately, 10 parts of propylene carbonate and 35 parts of propylene glycol were mixed together to form a mixture in which 0.5 parts of ketoprofen were dissolved. Then, 1.5 parts of hydroxypropylcellulose were dissolved in 25 parts of water, and the resulting solution was added to said swollen carboxyvinyl polymer and agitated until the polymer had been entirely hydrated. The whole so agitated was mixed with said solution of ketoprofen in the mixture of propylene carbonate and propylene glycol, incorporated with an aqueous solution of 0.5 parts of diisopropanolamine in 6.0 parts of water and then thoroughly agitated until the whole had been made homogeneous, thereby to obtain an anti-inflammatory and analgesic gel composition.

EXAMPLE 4

Two and a half (2.5) parts of carboxyvinyl polymer (the same as that used in Example 1) were swollen in 20 parts of water. Separately, 15 parts of propylene carbonate, 10 parts of propylene glycol and 20 parts of ethanol were mixed together to form a mixture in which 5 parts of ketoprofen were dissolved. Then, 2 parts of hydroxypropylcellulose were dissolved in 20 parts of ethanol, and the resulting solution was added to said swollen carboxyvinyl polymer and then agitated until the polymer had been entirely hydrated. The whole so agitated was incorporated with said solution of ketoprofen in the mixture of propylene carbonate, propylene glycol and ethanol, further incorporated with an aqueous solution of 0.3 parts of triethanolamine in 5.2 parts of water and then agitated until the whole had been made homogeneous, thereby to obtain an anti-inflammatory and analgesic gel composition.

EXAMPLE 5

One and a half (1.5) parts of carboxyvinyl polymer (Carbopol 940 produced by Goodrich Chemical Co.) were swollen in 20 parts of water. Separately, 10 parts of propylene carbonate and 35 parts of propylene glycol were mixed together to form a mixture in which 1 part of flurbiprofen was dissolved. Then, 2 parts of hydroxypropylcellulose were dissolved in 20 parts of ethanol, and the resulting solution was added to said swollen carboxyvinyl polymer and then agitated until the polymer had been entirely hydrated. The whole so agitated was incorporated with said solution of flurbiprofen in the mixture of propylene carbonate and propylene glycol, further incorporated with an aqueous solution of 0.2 parts of triethaolamine in 10.3 parts of water and then thoroughly agitated until the whole had been made homogeneous, thereby obtaining an anti-inflammatory and analgesic gel composition.

EXAMPLE 6

Two parts of carboxyvinyl polymer (Hiviswako 104 produced by Wako Junyaku Kogyo Co., Ltd.) were swollen in 20 parts of water. Separately, 15 parts of propylene carbonate and 20 parts of propylene glycol were mixed together to form a mixture in which 3 parts of flurbiprofen were dissolved. Then, 2 parts of hydroxypropylcellulose were dissolved in 30 parts of ethanol, and the resulting solution was added to said swollen carboxyvinyl polymer and agitated until the polymer had been entirely hydrated. The whole so agitated was incorporated with said solution of flurbiprofen in the mixture of propylene carbonate and propylene glycol, further incorporated with an aqueous solution of 0.2 parts of triethanolamine in 7.8 parts of water and then thoroughly agitated until the whole had been made homogeneous, thereby obtaining an anti-inflammatory and analgesic gel composition.

EXAMPLE 7

One and a half (1.5) parts of carboxyvinyl polymer (the same as that used in Example 1) were swollen in 20 parts of water. Separately, 10 parts of propylene carbonate and 35 parts of propylene glycol were mixed together to form a mixture in which 0.5 parts of flurbiprofen were dissolved. Then, 1.5 parts of hydroxypropylcellulose were dissolved in 25 parts of water to form a solution which was added to said swollen carboxyvinyl polymer and agitated until the polymer had been entirely hydrated. The whole so agitated was incorporated with said solution of flurbiprofen in the mixture of propylene carbonate and propylene glycol, further incorporated with an aqueous solution of 0.5 parts of diisopropanolamine in 6.0 parts of water and then thoroughly agitated until the whole had been made homogeneous, thereby to obtain an anti-inflammatory and analgesic gel composition.

EXAMPLE 8

Two and a half (2.5) parts of carboxyvinyl polymer (the same as that used in Example 1) were swollen in 20 parts of water. Separately, 15 parts of propylene carbonate, 10 parts of propylene glycol and 20 parts of ethanol were mixed together to form a mixture wherein 5 parts of flurbiprofen were dissolved. Then, 2 parts of hydroxypropylcellulose were dissolved in 20 parts of ethanol, and the resulting solution was added to said swollen carboxyvinyl polymer and agitated until the polymer had been entirely hydrated. The whole so agitated was incorporated with said solution of flurbiprofen in the mixture of propylene carbonate, propylene glycol and ethanol, further incorporated with an aqueous solution of 0.3 parts of triethanolamine in 5.2 parts of water and then thoroughly agitated until the whole had been made homogeneous, thereby obtaining an anti-inflammatory and analgesic gel composition.

EXAMPLE 9

One and a half (1.5) grams of a carboxyvinyl polymer (produced under the trademark of Carbopol 940 by Goodrich Chemical Corp.) were swollen in 300 g of water. Separately, 10 g of propylene carbonate and 5 g of propylene glycol were mixed together to form a mixture in which 1 g of ketoprofen was dissolved. Then, 2 g of hydroxypropylcellulose were dissolved in 44 g of ethanol, added to said swollen carboxyvinyl polymer and agitated to an extent that the polymer had been entirely hydrated. The whole so agitated was mixed with said solution of ketoprofen in the mixture of the propylene carbonate and propylene glycol, incorporated with a solution of 0.2 g triethanolamine in 6.3 g water and thoroughly agitated until the resulting mixture had been made homogeneous, thereby to obtain an anti-inflammatory analgesic gel composition.

EXAMPLE 10

Two (2.0) grams of carboxyvinyl polymer (produced under the trademark of Hiviswako 104 by Wako Junyaku Kogyo Co., Ltd.) were swollen in 25 g of water. Separately, 10 g of propylene carbonate and 5 g of propylene glycol were mixed together to form a mixture in which 3 g of ketoprofen were dissolved. Then, a solution of 2 g hydroxypropylcellulose in 44 g ethanol was added to said carboxyvinyl polymer so swollen and agitated until the polymer had been entirely hydrated. The whole so agitated was mixed with said ketoprofen dissolved in the propylene carbonate-propylene glycol mixture, incorporated with a solution of 0.2 g ethanolamine in 8.8 g water and then thoroughly agitated until the resulting mixture had wholly been made homogeneous, thereby to obtain an anti-inflammatory analgesic gel composition.

EXAMPLE 11

Five (5) grams of ketoprofen were dissolved in a mixture of 44 g ethanol, 5 g propylene glycol and 10 g propylene carbonate and then incorporated with 2.3 g of hydroxypropylcellulose. The whole was incorporated with 2.2 g of a carboxyvinyl polymer (same as used in Example 10) swollen in 25 g of water and agitated until the polymer had been entirely hydrated. The whole so agitated was incorporated with a solution of 0.3 g triethanolamine in 6.2 g water and then thoroughly agitated until the resulting mixture had wholly been made homogeneous, thereby to obtain an anti-inflammatory analgesic gel composition.

EXAMPLE 12

Three (3) grams of ketoprofen were dissolved in a mixture of 40 g ethanol and 20 g propylene glycol to form a ketoprofen solution which was incorporated with 2.0 g of a carboxyvinyl polymer (same as used in Example 10) swollen in 23.9 g of water and agitated until the polymer had wholly been made homogeneous. The ketoprofen solution so incorporated and agitated was incorporated with a solution of 1.1 g diisopropanolamine in 10 g water and then thoroughly agitated until the whole had wholly been made homogeneous, thereby to obtain an anti-inflammatory analgesic gel composition.

EXAMPLE 13

Three (3) grams of ketoprofen were dissolved in a mixture of 40 g ethanol, 15 g propylene glycol and 10 g propylene carbonate to form a ketoprofen solution which was incorporated under agitation with 1.0 g of hydroxypropylcellulose. The whole was incorporated with 2 g of a carboxyvinyl polymer (same as used in Example 10) swollen in 18 g of water and agitated until the polymer had been entirely hydrated. The whole so incorporated and agitated was thoroughly agitated until the whole had been made homogeneous, thereby to obtain an anti-inflammatory analgesic gel composition.

EXAMPLE 14

Three (3) grams of ketoprofen were dissolved in a mixture of 40 g ethanol, 5 g polyoxyethylene (10) monolaurate, 10 g propylene glycol and 10 g propylene carbonate, incorporated with 2.2 g of a carboxyvinyl polymer (same as used in Example 10) swollen in 18.6 g of water and agitated until the polymer had been entirely hydrated. The whole was added to a solution of 1.2 g diisopropanolamine in 10 g of water and then thoroughly agitated until the resulting whole mass had been made homogeneous, thereby to obtain an anti-inflammatory analgesic gel composition.

EXAMPLE 15

Three (3) grams of ketoprofen were dissolved in a mixture of 20 g ethanol, 35 g propylene glycol and 10 g propylene carbonate and incorporated under agitation with 1.5 g of hydroxypropylcellulose. The whole was incorporated with 2.0 g of a carboxyvinyl polymer (same as used in Example 10) swollen in 18.1 g of water, agitated until the polymer had been entirely hydrated, incorporated with a solution of 0.4 g diisopropanolamine in 100 g of water and then thoroughly agitated until a homogeneous mass had been formed, thereby to obtain an anti-inflammatory analgesic composition.

EXAMPLE 16

Three (3) grams of ketoprofen were dissolved in a mixture of 40 g ethanol, 10 g polyoxyethylene (10) monolaurate, 6 g propylene glycol and 2 g diisopropyl adipate to form a ketoprofen solution which was incorporated with 2.3 g of a carboxyvinyl polymer (same as used in Example 10) swollen in 25.7 g of water and agitated until the polymer had been entirely hydrated. The whole was incorporated with 1.0 g of diisopropanolamine dissolved in 10 g of water and then thoroughly agitated until the resulting mixture had wholly been made homogeneous, thereby to obtain an anti-inflammatory analgesic gel composition.

EXAMPLE 17

Seven (7) grams of ketoprofen were dissolved in a mixture of 44 g ethanol, 10 g propylene glycol and 10 g propylene carbonate, incorporated under agitation with 2.4 g of hydroxypropylcellulose, further incorporated with 2.5 g of a carboxyvinyl polymer (same as used in Example 10) swollen in 18 g of water and agitated until the polymer had been entirely hydrated. The whole was incorporated with 0.4 g of triethanolamine dissolved in 5.7 g of water and then thoroughly agitated until the resulting mixture had wholly been mad homogeneous, thereby to obtain an anti-inflammatory analgesic gel composition.

Furthermore, the following reference example indicates a conventional gel composition for comparison with the gel composition of this invention in the following percutaneous absorption and pharmacological experiments.

REFERENCE EXAMPLE

One and a half (1.5) parts of carboxyvinyl polymer (the same as that used in Example 1) were swollen in 20 parts of water. Separately, 10 parts of propylene carbonate and 35 parts of propylene glycol were mixed together to form a mixture in which 1 part of indomethacin was dissolved. After this, the same procedure as in Example 1 was followed thereby to obtain an anti-inflammatory and analgesic gel composition.

The percutaneous absorption effects, anti-inflammatory effects and safety of the gel compositions of this invention will be substantiated by the following pharmacological experiments.

EXPERIMENT 1

Percutaneous absorption test

Five healthy male adults were used as subjects. In each adult, the skin of inner side of his forearm was defined by applying an adhesive tape on the skin to obtain 8 skin portions, each 1.4 cm × 1.4 cm in area, respectively defined by the adhesive tape. Then, microsyringes were filled with gels compositions containing 1% of ketoprofen, flurbiprofen and indomethacin in the same gel base, respectively, in accordance with the method of Lindsay C. et al. Twenty $\mu l$ (190 $\mu g$ as the medicine or effective ingredient) of each of the gel compositions were applied externally to said skin portion and then fixed directly by an adhesive tape. The adhesive tapes were peeled zero and 4 hours after the application and then inserted into 25-ml measuring flasks, respectively, while the gel compositions remaining on the skin portions were recovered, respectively, by pressing a funnel against the skin portions, pouring a small amount of methanol from the foot of the funnel to the skin portions to wash the remaining gel composition and repeating this washing procedure several times to recover the whole of the remaining composition in solution in methanol. In this case, methanol was used in such an amount that the methanol solution so recovered amounted to 25 ml. For the ketoprofen and flurbiprofen, 2 ml of their respective methanol solutions were diluted with 2 ml of methanol and then measured for absorbancy at a wavelength of 225 nm and 246 nm by the use of a double beam spectrophotometer produced by Shimadzu Seisakusho Co., Ltd. On the other hand, for the indomethacin, 25 ml of its methanol solution recovered were measured, without dilution, for absorbancy at a wavelength of 320 nm. Quantitative determination was made from a quantity inspection curve prepared from absorbancies for solution of the medicines having various known concentrations.

The percutaneous absorption ratio was calculated from the following formula:

$$\text{Absorption ratio (\%)} = 100 \times \left(1 - \frac{\text{Amount of medicine recovered 4 hours after the administration}}{\text{Amount of medicine recovered zero hour after the administration}}\right)$$

The test results are as shown in the following Table 1.

TABLE 1

| Gel composition tested | Amount of medicine absorbed 4 hours after administration |
| --- | --- |
| Gel composition of Example 1 (containing 1% of ketoprofen) | 48.3 ± 3.4 |
| Gel composition of Example 5 (containing 1% of flurbiprofen) | 49.2 ± 5.5 |
| Gel composition of Reference Example (containing 1% of indomethacin) | 11.5 ± 3.6 |

The above values are the mean values and standard errors for the five subjects.

EXPERIMENT 2

Topical anti-inflammatory activity on carrageenin-induced dorsal cutaneous edema in rats Male rats of Wister strain, weighing 90–110 g (four weeks old), were depilated with Eba Cream (tradename, a depilatory produced by Tokyo Tanabe Pharmaceutical Co., Ltd.) and allowed to stand overnight for use in the experiment. Then, 0.1 ml/site of a physiological salt solution containing 1% of carrageenin (Picnin A produced by Pasco International Co.) was hypodermally injected into one side of the dorsal skin of the rats, while 0.1 ml/site of a physiological salt solution (containing no carrageenin) was intradermally injected into the other dorsal side thereof, these sides being positioned symmetrically to each other with respect to the backbone of the rats. Soon after the injection of the carrageenin-containing solution, an adhesive plaster (for patch tests) containing 100 mg of the medicine to be tested was applied to each of the sites at which the carrageenin-containing solution was injected. The adhesive plaster used was the "Small size" one produced by Torii Pharmaceutical Co., Ltd. Two and a half (2.5) hours later, 0.5 ml/100 g (body weight) of a physiological salt solution containing 1% of pontamine sky blue (PSB) was intravenously injected to the tail of the rats, 30 minutes after which the rats so injected were allowed to die by bloodletting. The skin of the dead rats was peeled therefrom and immediately measured for thickness at the carrageenin injected site with a dial thickness gauge (pressure 40 g, manufactured by Ozaki Seisakusho Co., Ltd.). The swelling ratios (%) at the edema portion of the skin were calculated as follows:

$$\text{Swelling ratio (\%)} = \frac{\text{Thickness of skin at carrageenin injected site} - \text{Thickness of skin at physiological salt solution injected site}}{\text{Thickness of skin at physiological salt solution injected site}} \times 100$$

Further, the dye extravasating area was calculated by multiplying the longer diameter by the shorter diameter in the dye extravasating portion of the skin. Still further, the pontamine sky blue was extracted by the use of the Harada et al.'s method (Harada, M., Takeuchi, M., Fukao, T. and Katagiri, K.; J. Pharm. Pharmacol. 23, 218, 1971) and then measured for the amount of the extravasating dye by the use of a spectrophotometer.

The test results are as indicated in Table 2.

TABLE 2

| Gel composition tested | No. of animals tested | Swelling (%) | Dye extravasating area (cm²) | Amount of dye extravasated (μg) |
| --- | --- | --- | --- | --- |
| Control group (Gel base) | 7 | 73.9 ± 4.4 | 0.60 ± 0.06 | 10.5 ± 1.9 |
| Gel composition of Ex. 1 (containing 1% of Ketoprofen) | 8 | 51.8 ± 2.6** [30.0] | 0.16 ± 0.04** [73.3] | 5.1 ± 0.8* [51.9] |
| Gel composition of Ex. 2 (containing 3% of Ketoprofen) | 7 | 42.5 ± 2.4** [42.6] | 0.14 ± 0.03** [76.7] | 5.2 ± 0.7* [50.5] |
| Gel composition of Ex. 5 (containing 1% of flurbiprofen) | 7 | 52.9 ± 4.0** [28.4] | 0.20 ± 0.05** [66.7] | 5.3 ± 1.2* [49.5] |
| Gel composition of Ex. 6 (containing 3% of flurbiprofen) | 7 | 49.5 ± 2.9** [33.0] | 0.15 ± 0.05** [75.0] | 5.3 ± 0.7* [49.5] |
| Gel composition of Ref. Ex. (containing 1% of indomethacin) | 8 | 57.1 ± 3.2** [22.8] | 0.26 ± 0.04** [56.7] | 5.5 ± 0.6* [47.2] |

Notes:
(1) Each of the gel compositions to be tested was applied in an amount of 100 mg for 3 hours immediately after the intradermal injection of the solution containing 1% of carrageenin.
(2) Asterisks * and ** indicate $P < 0.05$ and $P < 0.01$ respectively, thereby to mean that there is a significant difference.
(3) Ex. = Example, Ref. Ex. = Reference Example
(4) The values in the parentheses indicate inhibition ratios with respect to the Control group (gel base).

TABLE 3

| Gel composition tested | No. of animals used | Swelling ratio (%) | Inhibition ratio (%) |
| --- | --- | --- | --- |
| Control group (Gel base) | 8 | 60.4 ± 2.1 | — |
| Gel composition of Ex. 1 (containing 1% of Ketoprofen) | 8 | 45.3 ± 2.8** | 25.0 |
| Gel composition of Ex. 2 (containing 3% Ketoprofen) | 8 | 39.8 ± 2.8** | 34.1 |
| Gel composition of Ex. 5 (containing 1% of flurbiprofen) | 8 | 47.9 ± 3.3** | 20.7 |
| Gel composition of Ex. 6 (containing 3% of flurbiprofen) | 8 | 46.4 ± 3.0** | 23.2 |
| Gel composition of Ref. Ex. | 8 | 51.0 ± 2.3** | 15.6 |

TABLE 3-continued

| Gel composition tested | No. of animals used | Swelling ratio (%) | Inhibition ratio (%) |
|---|---|---|---|
| (containing 1% of indomethacin) | | | |

Notes:
(1) One hundred (100) mg of each of the gel compositions to be tested were applied one time for 3 hours just before the fracture and another one time for 3 hours just after the fracture.
(2) Asterisks ** indicate P < 0.01 thereby to mean that there is a significant difference.
(3) Ex. = Example, Ref. Ex. = Reference Example
(4) Inhibition ratio was expressed with respect to control group (gel base).

EXPERIMENT 3

Topical anti-inflammatory activity on fracture edema at the hind leg portions of rats Male rats of Wister strain, weighing about 130 g (five weeks old), were used as the test animals.

One hundred (100) mg of the gel compositions shown in Table 3 were thoroughly rubbed into the left legs of the rats, and the leg skin portions to which the composition was applied were wrapped with a Saran wrap (Polyvinylidene type synthetic resin film produced by Asahi Dow Chemical Co.) to prevent the rats from licking the gel composition so applied. In addition, a disposable beaker was put on the head of the rats and fixed with a rubber tape to enclose the head in the beaker, for prevention from licking the applied medicine. Three hours later, the rats were anesthetized lightly with ether and then the test medicine-applied leg portions were held between Kocher forceps and subjected to cross linear fracture at the metatarsal bone, soon after which 100 mg of the gel composition were again applied to said leg portions and then treated in the same manner as above. Three hours after the fracture, the measurements were made as follows.

The volumes of the leg portions before the fracture and 3 hours thereafter were measured by the Fujihira's method (Fujihira, E: Applied Pharmacol. 5, 119, 1971), and the swelling ratios (%) were calculated as follows.

$$\text{Swelling ratio (\%)} = \frac{\text{leg volume 3 hours after the fracture} - \text{leg volume before the fracture}}{\text{leg volume before the fracture}} \times 100$$

The test results are as shown in Table 3.

EXPERIMENT 4

Anti-inflammatory activity on gastric mucous membrane troubles in rats

Male rats of Wister strain, each weighing about 200 g, were fasted except for unlimited feeding of water for a time period of 24 hours, after which each of the test compounds shown in Table 4 was administered to the rats so fasted. The test compound in the form of a gel composition was administered by applying a plaster for patch test (the plaster being coated with 0.1 ml of said gel composition) to the rat's back the hair of which had been shaved with an electric razor. The ketoprofen and indomethacin each in the powder form were suspended in an 0.5% tragacanth rubber-containing physiological saline solution and then orally administered to the test animals, respectively. Six hours after said administration, the test animals were slaughtered to remove their stomachs which were incised along the greater curvature thereof to visually observe whether or not an ulcer was formed at the gastric mucous membrane of their stomachs. The ulceration ratio (%) was calculated from the following equation:

$$\text{Ulceration ratio (\%)} = \frac{\text{No. of test animals having their stomach ulcerated}}{\text{No. of animals tested}} \times 100$$

The test results are as shown in Table 4.

TABLE 4

| Test compound | Method of administration | No. of animals tested | Ulceration ratio (%) |
|---|---|---|---|
| Control | — | 6 | 0 |
| Gel composition of Example 2 (ketoprofen content: 3%) | Percutaneous | 6 | 0 |
| Indomethacin ointment (indomethacin content: 1%) | Percutaneous | 6 | 33.3 |
| Ketoprofen powder (5 mg/Kg) | Oral | 6 | 100.0 |
| Indomethacin powder (1 mg/Kg) | Oral | 6 | 100.0 |

It is seen from the above test results that the ulceration ratios for the ketoprofen and indomethacin powders orally administered were 100% respectively and that the ulceration ratio for the indomethacin ointment percutaneously administered was 33.3%.

On the other hand, Table 4 indicates that the ulceration ratio for the ketoprofen gel composition of the present invention was zero, that is, the formation of ulcers was not appreciated at all. This is an unexpected fact which will be helpful in eliminating side effects (gastrointestinal troubles) caused by non-steroid preparations, the side effects being now taken up very often as a problem to be solved. In addition, this fact also proved the safety and usefulness of the ketoprofen gel composition as well as high superiority thereof to the indomethacin ointment.

EXPERIMENT 5

Test for toxicity

A group of 10 mice consisting of male and female ones of ddy strain, each weighing 19–26 g, and a group of 10 rats consisting of male and female ones of Wister strain, each weighing 102–130 g, were used as the test animals. Test compounds (in the forms of gel compositions containing 3% ketoprofen and 3% flurbiprofen, respectively) shown in Table 5 were coated on the test animals' backs the hair of which had been shaved with an electric razor, in amounts of 15,000 mg/Kg which was the maximum coatable amount for the test compounds in the forms of gel compositions, respectively, to find how many of the test animals died during 14 days after the coating of the test compounds. The results are as shown in Table 5.

TABLE 5

| Test compound | Test animal | Sex | No. of dead animals/ No. of animals tested | Percutaneous $LD_{50}$ (mg/Kg) |
|---|---|---|---|---|
| Ketoprofen (in the form of a gel composition containing 3% ketoprofen) | Mice | ♂ | 0/10 | >15000 |
| | | ♀ | 0/10 | >15000 |
| | Rats | ♂ | 0/10 | >15000 |
| | | ♀ | 0/10 | >15000 |

TABLE 5-continued

| Test compound | Test animal | Sex | No. of dead animals/ No. of animals tested | Percutaneous LD$_{50}$ (mg/Kg) |
|---|---|---|---|---|
| Flurbiprofen | Mice | ♂ | 0/10 | >15000 |
| (in the form of a gel | | ♀ | 0/10 | >15000 |
| composition containing | Rats | ♂ | 0/10 | >15000 |
| 3% flurbiprofen) | | ♀ | 0/10 | >15000 |

It is seen from Table 5 that none of the test animals died during the test even in cases where they were coated on the hair-shaved back with the test compound in an amount of 15,000 mg/Kg which was the maximum coatable amount. This proves that ketoprofen and flurbioprofen in the gel composition form are harmless and safe to animals when externally applied.

EXPERIMENT 6

Patch test on healthy human beings

Twenty-five (25) male people were subjected to patch test in accordance with the test method proposed by Kawamura et al. [Taro Kawamura et al.: Nippi Kaishi (Journal of Japanese Dermatology), 80, 301, 1969]. More particularly, plasters for the patch test which were coated with 0.1 ml of the test compounds respectively as shown in Table 7, were applied to the male subjects in the inner side of their upper arm and maintained there for 24 hours respectively. The plasters so applied were peeled to visually observe the conditions of the upper arm portion (from which the patch had been peeled) 30 minutes and 24 hours after the peeling in accordance with the criteria as shown in Table 6. The results are as shown in Table 7.

TABLE 6

| Score | |
|---|---|
| — | No extraordinary reaction |
| ± | Slight erythema |
| + | Erythema or Papule |
| ++ | Erythema and Swelling; or Erythema and Papule |
| +++ | Erythema, Swelling and small vesicle; or Erythema, Swelling and Papule |
| ++++ | Vesicle and Erosion |

TABLE 7

| | Observations Positivity (%), determined on the basis of the score ± or higher being assumed positive. | |
|---|---|---|
| Test compound | 30 minutes later | 24 hours later |
| Gel composition of Example 2 (ketoprofen content: 3%) | 4.5 (1/22) | 4.5 (1/22) |
| Gel composition of Example 6 (flurbiprofen content: 3%) | 4.0 (1/25) | 4.0 (1/25) |
| Indomethacin ointment (indomethacin content: 1%) | 56.0** (14/25) | 44.0** (11/25) |

The double asterisk ** indicates that a significant difference exists at P < 0.01 between the two.

As is seen from the results in Table 7, the indomethacin ointment caused a considerable amount of erythema, papule, swelling, etc., while the ketoprofen or flurbiprofen gel composition caused a very small amount of slight erythema and erythema only. This proves that the ketoprofen and flurbiprofen gel compositions are excellently safe to human bodies.

It has been found from the aforementioned pharmacological experiments that the gel compositions of this invention are very excellent in percutaneous absorption and medicinal efficacy as well as in safety.

What is claimed is:

1. An anti-inflammatory and analgesic gel composition comprising, by weight, 0.5–10% of ketoprofen as the effective ingredient, 2–40% of a glycol selected from the group consisting of propylene glycol, butylene glycol, polyethylene glycol, polypropylene glycol, polyethylene glycol dodecyl ether and glycerine, 20–55% of water, up to 60% of a lower alcohol selected from the group consisting of ethanol, denatured ethanol, propanol and isopropanol, 0.5–5% of a gelling agent selected from the group consisting of carboxyvinyl polymers, hydroxycellulose, methylcellulose, carboxymethylcellulose, hydroxypropylcellulose and alginic acid-propylene glycol ester and 0.1–3% of a neutralizing agent selected from the group consisting of triethanolamine, diethylamine, triethylamine, diisopropylamine and diisopropanolamine.

2. An anti-inflammatory and analgesic gel composition according to claim 1, further comprising up to 20% by weight of a solubilizing agent selected from the group consisting of propylene carbonate, diethyl sebacate, benzyl alcohol and diisopropyl adipate.

3. An anti-inflammatory and analgesic gel composition according to claim 2, further comprising up to 15% by weight of a surface-active agent selected from the group consisting of sesquioleic acid sorbitan, trioleic acid sorbitan, monooleic acid sorbitan, monostearic acid polyethylene glycol, monooleic polyoxyethylenesorbitan, monolauric acid polyoxyethylenesorbitan, polyoxyethylene nonylphenyl ether, polyoxyethylenecetyl ether, polyoxyethylenelauryl ether and mixtures thereof.

4. An anti-inflammatory analgesic gel composition according to claim 1, 2 or 3, characterized in that it is kept at a pH value of 4.5–7.0.

5. A method of improving the anti-inflammatory analgesic effects obtainable with the gel composition of claim 1, 2, or 3 which comprises topically applying said composition to the skin of animals and human beings.

6. A method according to claim 1, wherein the gel composition is kept at a pH value of 4.5–7.0.

7. A method of improving the anti-inflammatory analgesic effects of an inflammatory analgesic gel compositions which comprises topically applying said composition to the skin of animals and human beings, the gel composition comprising, by weight, 0.5–10% of ketoprofen as the effective ingredient, 2–40% of a glycol selected from the group consisting of propylene glycol, butylene glycol, polyethylene glycol, polypropylene glycol, polyethylene glycol dodecyl ether and glycerine, 20–55% of water, up to 60% of a lower alcohol selected from the group consisting of ethanol, denatured ethanol, propanol and isopropanol, 0.5–5% of a gelling agent selected from the group consisting of carboxyvinyl polymers, hydroxyethylcellulose, methylcellulose, carboxymethylcellulose, hydroxypropylcellulose and alginic acid-propylene glycol ester and 0.1–3% of a neutralizing agent selected from the group consisting of triethanolamine, diethylamine, triethylamine, diisopropylamine and diisopropanolamine.

8. A method according to claim 7, wherein the gel composition further comprises up to 20% by weight of a solubilizing agent selected from the group consisting of propylene carbonate, diethyl sebacate, diisopropyl adipate and bezyl alcohol.

9. A method according to claim 8, wherein the gel composition further comprises up to 15% by weight of a surface-active agent selected from the group consisting of sesquioleic acid sorbitan, trioleic acid sorbitan, monooleic acid sorbitan, monostearic acid sorbitan, monolauric acid sorbitan, monostearic acid polyethylene glycol, monooleic acid polyoxyethylenesorbitan, monolauric acid polyoxyethylenesorbitan, polyoxyethylenenonylphyenyl ether, polyoxyethylenecetyl ether, polyoxyethylenelauryl ether and mixtures thereof.

10. An anti-inflammatory and analgesic gel composition according to claim 1, wherein the alcohol is comprises in an amount by weight of 20-45%.

11. An anti-inflammatory and analgesic gel composition according to claim 4, characterized in that the pH value is in the range of 5.0-6.5.

12. A method of improving the anti-inflammatory analgesic effects according to claim 5, wherein the alcohol is comprised in an amount by weight of 20-45% in the gel composition.

13. A method of improving the anti-inflammatory analgesic effects according to claim 7, wherein the alcohol is comprised in an amount by weight of 20-45% in the gel composition.

14. A method according to claim 6, wherein the pH value is in the range of 5.0-6.5%.

15. An anti-inflammatory and analgesic gel composition comprising by weight, 3-7% of ketoprofen as the effective ingredient 2-40% of a glycol selected from the group consisting of propylene glycol, butylene glycol, polyethylene glycol, polypropylene glycol, polyethylene glycol dodecyl ether and glycerine, 20-55% of water, up to 60% of a lower alcohol selected from the group consisting of ethanol, denatured ethanol, propanol and isopropanol, 0.5-5% of a gelling agent selected from the group consisting of carboxyvinyl polymers, hydroxyethylcellulose, methylcellulose, carboxymethylcellulose, hydroxypropylcellulose and alginic acid-propylene glycol ester and 0.1-3% of a neutralizing agent selected from the group consisting of triethanolamine, diethylamine, triethylamine, diisopropylamine and diisopropanolamine.

* * * * *